(12) United States Patent
Brannan

(10) Patent No.: US 9,987,087 B2
(45) Date of Patent: Jun. 5, 2018

(54) STEP-DOWN COAXIAL MICROWAVE ABLATION APPLICATORS AND METHODS FOR MANUFACTURING SAME

(71) Applicant: Covidien LP, Mansfield, MA (US)

(72) Inventor: Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 441 days.

(21) Appl. No.: 14/228,818

(22) Filed: Mar. 28, 2014

(65) Prior Publication Data
US 2014/0296839 A1    Oct. 2, 2014

Related U.S. Application Data

(60) Provisional application No. 61/969,545, filed on Mar. 24, 2014, provisional application No. 61/806,605, filed on Mar. 29, 2013.

(51) Int. Cl.
*A61B 18/18* (2006.01)
*A61B 17/00* (2006.01)
*A61B 18/00* (2006.01)

(52) U.S. Cl.
CPC ...... *A61B 18/1815* (2013.01); *A61B 2017/00526* (2013.01); *A61B 2018/00577* (2013.01); *A61B 2018/1892* (2013.01); *Y10T 156/10* (2015.01)

(58) Field of Classification Search
CPC .................. A61B 18/18; A61B 2018/1892
See application file for complete search history.

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 A | 6/1995 |
| DE | 390937 C | 3/1924 |

(Continued)

OTHER PUBLICATIONS

International Preliminary Report on Patentability issued in corresponding International Application No. PCT/US2014/032164, dated Sep. 29, 2015.

(Continued)

*Primary Examiner* — Ronald Hupczey, Jr.

(57) ABSTRACT

Microwave ablation applicators and methods for manufacturing the microwave ablation applicators are disclosed. A microwave ablation applicator includes a feed-line segment, a step-down segment, and a radiator base segment. The feed-line segment includes a first inner conductor, a first dielectric disposed on the first inner conductor, and a first outer conductor disposed on the first dielectric. The step-down segment includes a second inner conductor, a second dielectric disposed on the second inner conductor, and a second outer conductor disposed on the second dielectric. The radiator base segment includes a third inner conductor disposed on the third inner conductor, a third outer conductor disposed on the proximal end of the third dielectric so as to form a feed gap at a distal end of the radiator base segment, a balun dielectric disposed on the third outer conductor, and a balun outer conductor disposed on the balun dielectric.

11 Claims, 9 Drawing Sheets

(56) References Cited

U.S. PATENT DOCUMENTS

| | | |
|---|---|---|
| D266,842 S | 11/1982 | Villers et al. |
| D278,306 S | 4/1985 | McIntosh |
| 4,583,589 A | 4/1986 | Kasevich |
| D295,893 S | 5/1988 | Sharkany et al. |
| D295,894 S | 5/1988 | Sharkany et al. |
| 4,896,671 A | 1/1990 | Cunningham et al. |
| 5,301,687 A * | 4/1994 | Wong ............... A61B 18/1815 606/33 |
| 5,364,392 A | 11/1994 | Warner et al. |
| 5,370,644 A | 12/1994 | Langberg |
| D354,218 S | 1/1995 | Van de Peer |
| 5,545,137 A | 8/1996 | Rudie et al. |
| 5,563,376 A * | 10/1996 | Hansell, III ....... H01B 13/0006 156/53 |
| 5,603,697 A | 2/1997 | Grundy et al. |
| 5,624,392 A | 4/1997 | Saab |
| 5,685,839 A | 11/1997 | Edwards et al. |
| 5,693,082 A | 12/1997 | Warner et al. |
| 5,741,249 A | 4/1998 | Moss et al. |
| 5,980,505 A | 11/1999 | Wilson |
| 5,993,447 A | 11/1999 | Blewett et al. |
| 5,995,875 A | 11/1999 | Blewett et al. |
| 6,014,581 A | 1/2000 | Whayne et al. |
| D424,693 S | 5/2000 | Pruter |
| D424,694 S | 5/2000 | Tetzlaff et al. |
| D425,201 S | 5/2000 | Tetzlaff et al. |
| 6,061,551 A | 5/2000 | Sorrells et al. |
| 6,106,524 A | 8/2000 | Eggers et al. |
| 6,117,101 A | 9/2000 | Diederich et al. |
| 6,139,527 A | 10/2000 | Laufer et al. |
| 6,186,978 B1 | 2/2001 | Samson et al. |
| 6,210,367 B1 | 4/2001 | Carr |
| 6,235,024 B1 | 5/2001 | Tu |
| 6,277,113 B1 | 8/2001 | Berube |
| D449,886 S | 10/2001 | Tetzlaff et al. |
| 6,355,016 B1 | 3/2002 | Bagaoisan et al. |
| D457,958 S | 5/2002 | Dycus et al. |
| D457,959 S | 5/2002 | Tetzlaff et al. |
| 6,398,781 B1 | 6/2002 | Goble et al. |
| 6,485,486 B1 | 11/2002 | Trembly et al. |
| 6,496,737 B2 | 12/2002 | Rudie et al. |
| 6,496,738 B2 | 12/2002 | Carr |
| 6,514,249 B1 | 2/2003 | Maguire et al. |
| 6,547,788 B1 | 4/2003 | Maguire et al. |
| 6,575,969 B1 | 6/2003 | Rittman, III et al. |
| 6,599,288 B2 | 7/2003 | Maguire et al. |
| 6,629,974 B2 | 10/2003 | Penny et al. |
| 6,635,055 B1 | 10/2003 | Cronin |
| 6,652,515 B1 | 11/2003 | Maguire et al. |
| 6,676,657 B2 | 1/2004 | Wood |
| D487,039 S | 2/2004 | Webster et al. |
| 6,706,040 B2 | 3/2004 | Mahon et al. |
| 6,723,091 B2 | 4/2004 | Goble et al. |
| 6,740,108 B1 | 5/2004 | Just et al. |
| 6,770,070 B1 | 8/2004 | Balbierz |
| 6,780,183 B2 | 8/2004 | Jimenez, Jr. et al. |
| D496,997 S | 10/2004 | Dycus et al. |
| D499,181 S | 11/2004 | Dycus et al. |
| 6,847,848 B2 | 1/2005 | Sterzer et al. |
| 6,869,431 B2 | 3/2005 | Maguire et al. |
| 6,893,436 B2 | 5/2005 | Woodard et al. |
| 6,932,776 B2 | 8/2005 | Carr |
| 6,997,925 B2 | 2/2006 | Maguire et al. |
| 7,004,938 B2 | 2/2006 | Ormsby et al. |
| 7,047,068 B2 | 5/2006 | Haissaguerre |
| 7,049,068 B2 | 5/2006 | Thorp et al. |
| D525,361 S | 7/2006 | Hushka |
| 7,089,063 B2 | 8/2006 | Lesh et al. |
| 7,113,832 B2 | 9/2006 | Longo |
| D531,311 S | 10/2006 | Guerra et al. |
| D533,942 S | 12/2006 | Kerr et al. |
| D535,027 S | 1/2007 | James et al. |
| 7,197,356 B2 | 3/2007 | Carr |
| D541,418 S | 4/2007 | Schechter et al. |
| 7,200,445 B1 | 4/2007 | Dalbec et al. |
| D541,938 S | 5/2007 | Kerr et al. |
| 7,261,001 B2 | 8/2007 | Heijnsdijk et al. |
| 7,263,398 B2 | 8/2007 | Carr |
| 7,275,547 B2 | 10/2007 | Willis |
| 7,285,116 B2 | 10/2007 | de la Rama et al. |
| 7,294,125 B2 | 11/2007 | Phalen et al. |
| 7,300,436 B2 | 11/2007 | Penny et al. |
| 7,303,558 B2 | 12/2007 | Swanson |
| D564,662 S | 3/2008 | Moses et al. |
| 7,402,168 B2 | 7/2008 | Sanderson et al. |
| 7,410,486 B2 | 8/2008 | Fuimaono et al. |
| D576,932 S | 9/2008 | Strehler |
| 7,438,712 B2 | 10/2008 | Chouinard |
| 7,460,898 B2 | 12/2008 | Brister et al. |
| 7,467,015 B2 | 12/2008 | van der Weide |
| 7,507,229 B2 | 3/2009 | Hewitt et al. |
| D594,736 S | 6/2009 | Esjunin |
| D594,737 S | 6/2009 | Kelly et al. |
| 7,608,056 B2 | 10/2009 | Kennedy, II |
| 7,611,508 B2 | 11/2009 | Yang et al. |
| D606,203 S | 12/2009 | Husheer et al. |
| D613,412 S | 4/2010 | DeCarlo |
| 7,697,972 B2 | 4/2010 | Verard et al. |
| 7,706,894 B2 | 4/2010 | Stewart et al. |
| 7,713,259 B2 | 5/2010 | Gosiengfiao et al. |
| 7,722,604 B2 | 5/2010 | Brown, III et al. |
| 7,734,330 B2 | 6/2010 | Carr |
| 7,769,469 B2 | 8/2010 | Carr et al. |
| 7,824,392 B2 | 11/2010 | Zhou |
| 7,826,904 B2 | 11/2010 | Appling et al. |
| 7,833,218 B2 | 11/2010 | Lunn et al. |
| D634,010 S | 3/2011 | DeCarlo |
| 7,921,855 B2 | 4/2011 | Danek et al. |
| 7,933,660 B2 | 4/2011 | Carr |
| 7,993,351 B2 | 8/2011 | Worley et al. |
| 8,021,351 B2 | 9/2011 | Boldenow et al. |
| 8,075,532 B2 | 12/2011 | Kassab et al. |
| 8,182,466 B2 | 5/2012 | Stehr et al. |
| 8,206,373 B2 | 6/2012 | Zhou |
| 8,206,380 B2 | 6/2012 | Lenihan et al. |
| 8,226,566 B2 | 7/2012 | Nita |
| 8,277,438 B2 | 10/2012 | Griffin et al. |
| 8,289,551 B2 | 10/2012 | Wu |
| 8,292,881 B2 | 10/2012 | Brannan et al. |
| 8,328,799 B2 | 12/2012 | Brannan |
| 8,328,800 B2 | 12/2012 | Brannan |
| 8,328,801 B2 | 12/2012 | Brannan |
| 8,340,740 B2 | 12/2012 | Holzer et al. |
| 8,343,145 B2 | 1/2013 | Brannan |
| 8,394,092 B2 | 3/2013 | Brannan |
| 8,412,306 B2 | 4/2013 | Kurpad et al. |
| D681,810 S | 5/2013 | DeCarlo |
| 8,491,579 B2 | 7/2013 | Rossetto |
| 8,515,554 B2 | 8/2013 | Carr |
| 8,655,454 B2 | 2/2014 | Prakash et al. |
| 8,672,932 B2 | 3/2014 | van der Weide et al. |
| 8,795,268 B2 | 8/2014 | Willyard |
| 2002/0022836 A1 | 2/2002 | Goble et al. |
| 2003/0191451 A1 | 10/2003 | Gilmartin |
| 2005/0015081 A1 | 1/2005 | Turovskiy et al. |
| 2005/0115738 A1 * | 6/2005 | Yamaguchi ........ H01B 11/1813 174/102 R |
| 2005/0215942 A1 | 9/2005 | Abrahamson et al. |
| 2006/0009833 A1 | 1/2006 | Chobotov et al. |
| 2006/0089637 A1 | 4/2006 | Werneth et al. |
| 2006/0167416 A1 | 7/2006 | Mathis et al. |
| 2006/0241564 A1 | 10/2006 | Corcoran et al. |
| 2006/0253102 A1 | 11/2006 | Nance et al. |
| 2006/0282069 A1 | 12/2006 | Prakash et al. |
| 2007/0088319 A1 | 4/2007 | Martone |
| 2007/0287912 A1 | 12/2007 | Khuri-Yakub et al. |
| 2008/0091169 A1 | 4/2008 | Heideman et al. |
| 2008/0147056 A1 | 6/2008 | van der Weide et al. |
| 2008/0208039 A1 | 8/2008 | Kurpad et al. |
| 2008/0228167 A1 | 9/2008 | Mittermeyer et al. |
| 2008/0255507 A1 | 10/2008 | Mushtaha |
| 2009/0005766 A1 | 1/2009 | Brannan |
| 2009/0076409 A1 | 3/2009 | Wu et al. |
| 2009/0187180 A1 | 7/2009 | Brannan |

(56) References Cited

U.S. PATENT DOCUMENTS

| | | |
|---|---|---|
| 2009/0222002 A1 | 9/2009 | Bonn et al. |
| 2009/0234220 A1 | 9/2009 | Maschke |
| 2010/0036369 A1 | 2/2010 | Hancock |
| 2010/0262134 A1 | 10/2010 | Jensen et al. |
| 2010/0268196 A1 | 10/2010 | Hastings et al. |
| 2010/0305559 A1 | 12/2010 | Brannan et al. |
| 2011/0004205 A1 | 1/2011 | Chu et al. |
| 2011/0066144 A1 | 3/2011 | Bonn et al. |
| 2011/0130750 A1 | 6/2011 | Ormsby et al. |
| 2011/0166518 A1 | 7/2011 | Nguyen et al. |
| 2011/0166519 A1 | 7/2011 | Nguyen et al. |
| 2011/0196362 A1 | 8/2011 | Rossetto |
| 2011/0282336 A1* | 11/2011 | Brannan ............ A61B 18/1815 606/33 |
| 2011/0301587 A1 | 12/2011 | Deem et al. |
| 2011/0319880 A1 | 12/2011 | Prakash et al. |
| 2012/0065481 A1 | 3/2012 | Hunter et al. |
| 2012/0071822 A1 | 3/2012 | Romo et al. |
| 2012/0078175 A1 | 3/2012 | Vreeman |
| 2012/0078230 A1 | 3/2012 | Lowe et al. |
| 2012/0259326 A1 | 10/2012 | Brannan et al. |
| 2012/0277730 A1 | 11/2012 | Salahieh et al. |
| 2013/0137977 A1 | 5/2013 | Eder |
| 2013/0197481 A1 | 8/2013 | Guo et al. |
| 2013/0197482 A1 | 8/2013 | Akitomo |
| 2013/0237980 A1 | 9/2013 | Brannan |
| 2013/0241769 A1 | 9/2013 | Brannan et al. |
| 2013/0245624 A1 | 9/2013 | Bahney |
| 2013/0253500 A1 | 9/2013 | Lee et al. |
| 2013/0261617 A1 | 10/2013 | Podhajsky |
| 2013/0261620 A1 | 10/2013 | Brannan et al. |
| 2013/0267946 A1 | 10/2013 | Brannan et al. |
| 2013/0289560 A1 | 10/2013 | Decarlo et al. |
| 2013/0296841 A1 | 11/2013 | Brannan |
| 2013/0304057 A1 | 11/2013 | Rossetto |
| 2013/0317407 A1 | 11/2013 | Reid, Jr. et al. |
| 2013/0317495 A1 | 11/2013 | Brannan |
| 2013/0317499 A1 | 11/2013 | Brannan et al. |
| 2013/0324910 A1 | 12/2013 | Ohri et al. |
| 2013/0324911 A1 | 12/2013 | Ohri et al. |
| 2013/0338661 A1 | 12/2013 | Behnke, II |
| 2013/0345541 A1 | 12/2013 | Nau, Jr. |
| 2013/0345551 A1 | 12/2013 | Arts et al. |
| 2013/0345552 A1 | 12/2013 | Arts et al. |
| 2013/0345553 A1 | 12/2013 | Arts et al. |
| 2013/0345699 A1 | 12/2013 | Brannan et al. |
| 2014/0000098 A1 | 1/2014 | Dunning et al. |
| 2014/0005655 A1 | 1/2014 | Brannan |
| 2014/0005657 A1 | 1/2014 | Brannan et al. |
| 2014/0018668 A1 | 1/2014 | Zheng et al. |
| 2014/0018677 A1 | 1/2014 | Sharonov |
| 2014/0018793 A1 | 1/2014 | Sharonov |
| 2014/0046175 A1 | 2/2014 | Ladtkow et al. |
| 2014/0094789 A1 | 4/2014 | Brannan |
| 2014/0094792 A1 | 4/2014 | Sharonov |
| 2014/0094794 A1 | 4/2014 | Orszulak |
| 2014/0094797 A1 | 4/2014 | Brannan |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1034747 A1 | 9/2000 |
| EP | 1034748 | 9/2000 |
| EP | 1055400 | 11/2000 |
| EP | 1 159 926 A2 | 12/2001 |
| EP | 2147651 A1 | 1/2010 |
| EP | 2322113 A1 | 5/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| JP | 2009521967 A | 6/2009 |
| JP | 2010094518 A | 4/2010 |
| JP | 201136674 A | 2/2011 |
| JP | 2011251116 A | 12/2011 |
| JP | 2012139494 A | 7/2012 |
| JP | 2012250035 A | 12/2012 |
| KR | 20070093068 A | 9/2007 |
| KR | 20100014406 A | 2/2010 |

(56) References Cited

FOREIGN PATENT DOCUMENTS

| KR | 20120055063 A | 5/2012 |
|---|---|---|
| SU | 166452 | 11/1964 |
| SU | 401367 A1 | 10/1973 |
| SU | 727201 A2 | 4/1980 |
| WO | 94/16632 A1 | 8/1994 |
| WO | 97/24074 A1 | 7/1997 |
| WO | 00/36985 A2 | 6/2000 |
| WO | 0057811 A1 | 10/2000 |
| WO | 0100114 A1 | 1/2001 |
| WO | 02/45790 A2 | 6/2002 |
| WO | 2008/068485 A2 | 6/2008 |
| WO | 2010/035831 A1 | 4/2010 |
| WO | 2014025551 A1 | 2/2014 |

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSureTM Vessel Sealing System in Bloodless Hemorrhoidectomy" Innovations That Work, Mar. 2000.

(56) References Cited

OTHER PUBLICATIONS

Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Physics Medical 9(3), May/Jun. 1982
Magdy F. Iskander et al., "Design Optimization of Interstitial Antennas", IEEE Transactions on Biomedical Engineering, vol. 36, No. 2, Feb. 1989, pp. 238-246
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Intl Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shanga CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098; Oct. 14, 1993; Roger A. Stern.
U.S. Appl. No. 08/483,742; Jun. 7, 1995; Roger A. Stern.
U.S. Appl. No. 13/942,833, filed Jul. 16, 2013, Sharonov.
U.S. Appl. No. 14/011,414, filed Aug. 27, 2013, Ohri.

(56) References Cited

OTHER PUBLICATIONS

U.S. Appl. No. 14/011,438, filed Aug. 27, 2013, Ohri.
The Extended Search Report in corresponding European Application No. EP14774216, dated Oct. 10, 2016, 5 pages.
Chinese First Office Action for CN 201480008821.8 dated Nov. 21, 2016.
Japanese Office Action dated Mar. 13, 2018 and issued in Japanese Patent Application No. 2016-505587 with English translation.

* cited by examiner

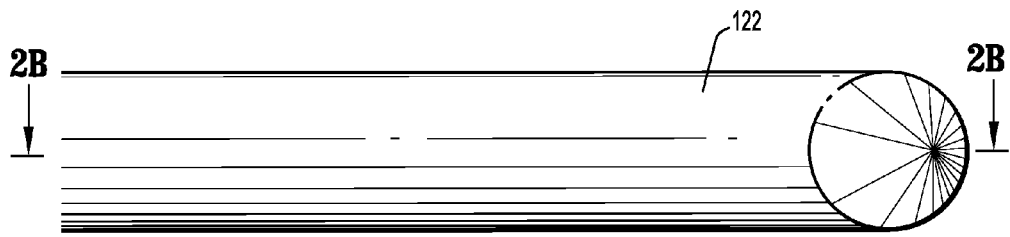
FIG. 2A
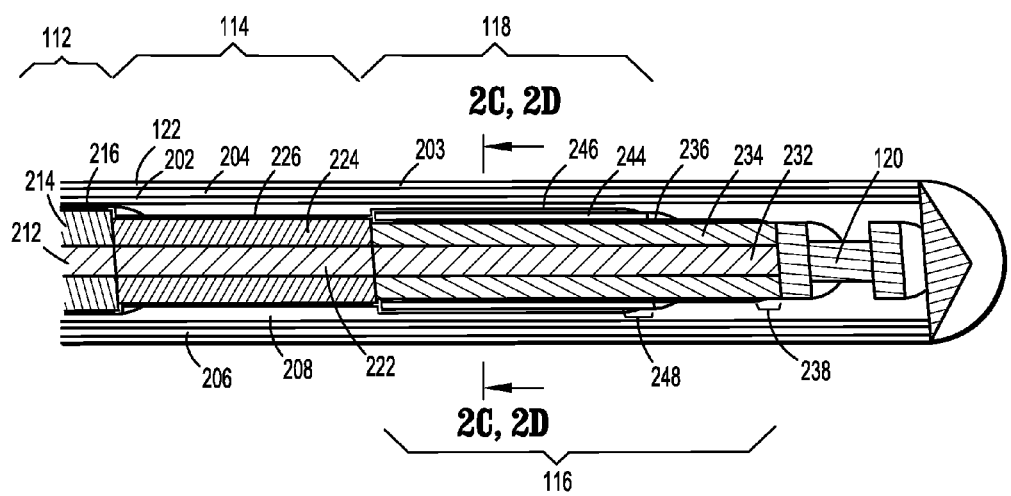
FIG. 2B
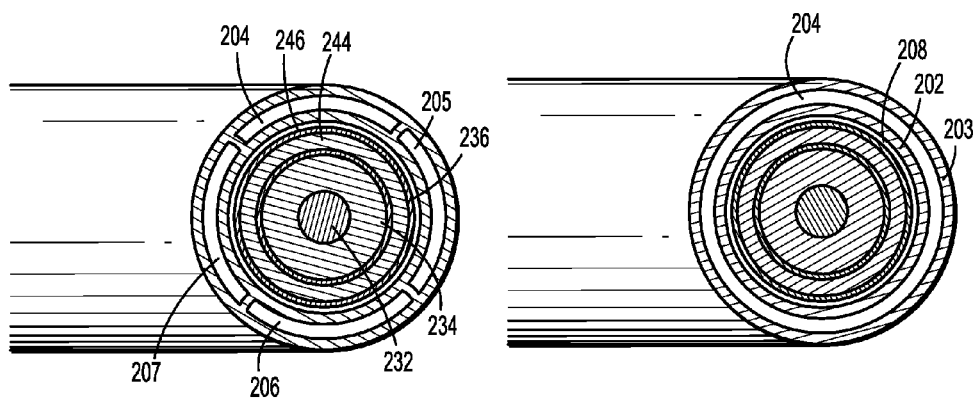
FIG. 2C  FIG. 2D

STEP-DOWN COAXIAL MICROWAVE ABLATION APPLICATORS AND METHODS FOR MANUFACTURING SAME

CROSS-REFERENCE TO RELATED APPLICATIONS

This application claims the benefit of and priority to U.S. Provisional Patent Application No. 61/806,605, filed on Mar. 29, 2013, and U.S. Provisional Patent Application No. 61/969,545, filed on Mar. 24, 2014, the entire contents of each of which are incorporated by reference herein for all purposes.

BACKGROUND

1. Technical Field

The present disclosure relates generally to microwave ablation applicators, and, more particularly, to reduced-size microwave ablation applicators and methods for manufacturing the same.

2. Discussion of Related Art

Electromagnetic fields can be used to heat and destroy tumor cells. Treatment may involve inserting ablation probes into tissues where cancerous tumors have been identified. Once the ablation probes are properly positioned, the ablation probes induce electromagnetic fields within the tissue surrounding the ablation probes.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source, and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

There are several types of microwave probes in use, e.g., monopole, dipole, and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The heating of tissue for thermal ablation is accomplished through a variety of approaches, including conduction of heat from an applied surface or element, ionic agitation by electrical current flowing from an electrode to a ground pad, optical wavelength absorption, or, in the case of microwave ablation, by dielectric relaxation of water molecules within an antenna electromagnetic field. The ablation zone can be broken down into two components: an active ablation zone and a passive ablation zone.

The active ablation zone is closest to the ablation device and encompasses the volume of tissue which is subjected to energy absorption high enough to assure thermal tissue destruction at a given application time in all but areas of very rapidly flowing fluids, such as around and within large blood vessels or airways. The active ablation zone size and shape is determined by ablation device design. The active ablation zone can therefore be used to produce predictable ablative effects over a given shape and volume of tissue.

The passive ablation zone surrounds the active zone and encompasses the volume of tissue which experiences a lower intensity of energy absorption. The tissue within the passive ablation zone may or may not experience tissue destruction at a given application time. Physiological cooling may counter heating from the lower level energy absorption and therefore not allow for sufficient heating to occur within the passive zone to kill tissue. Diseased or poorly perfused tissue within the passive zone may be more prone to heating than other tissues and may also be more susceptible to heat conduction from hotter areas within the ablation zone. The passive zone in these cases can result in unexpectedly large ablation zones. Due to these varying scenarios across space within a targeted physiology, relying on the passive zone to perform thermal ablation is challenging with unpredictable outcomes.

As electromagnetic fields can be induced at a distance by microwave probes, microwave ablation has the potential to create large active zones whose shapes can be determined and held constant by design. Furthermore, the shape and size can be determined through design to fit a specific medical application. By utilizing a predetermined active zone to create a predictable ablation zone, and not relying upon the indeterminate passive ablation zone, microwave ablation can provide a level of predictability and procedural relevance not possible with other ablative techniques.

The shape of the active zone about an antenna is determined by the frequency of operation, the geometry of the antenna, the materials of the antenna, and the medium surrounding the antenna. Operating an antenna in a medium of dynamically changing electrical properties, such as heating tissue, results in a changing shape of the electromagnetic field, and therefore a changing shape of the active zone. To maintain the shape of the active zone about a microwave antenna, the degree of influence on the electromagnetic field of the surrounding medium's electrical properties is reduced.

The size of the active zone about an antenna is determined by the amount of energy which can be delivered from the microwave generator to the antenna. With more energy delivered to the antenna, larger active zones can be generated. To maximize energy transfer from a microwave generator through waveguides and to a microwave antenna requires each system component to have the same impedance, or to be impedance matched. Whereas the impedance of the generator and waveguides are typically fixed, the impedance of a microwave antenna is determined by the frequency of operation, the geometry of the antenna, the materials of the antenna, and the medium surrounding the antenna. Operating an antenna in a medium of dynamically changing electrical properties, such as within heating tissue, results in a changing antenna impedance and varied energy delivery to the antenna, and, as a result, a changing size of the active zone. To maintain the size of the active zone about a microwave antenna, the degree of influence on the antenna impedance of the surrounding medium's electrical properties must be reduced.

In thermal ablation, the primary cause of active zone size and shape change is an elongation of the electromagnetic wave. Wavelength elongation occurs in heating tissue due to tissue dehydration. Dehydration reduces the dielectric constant, elongating the wavelength of microwave fields. Wavelength elongation is also encountered when a microwave device is used across various tissue types due to the varying dielectric constant between tissue types. For example, an electromagnetic wave is significantly longer in lung tissue than in liver tissue.

Wavelength elongation compromises the focus of microwave energy on the targeted tissue. With large volume ablation, a generally spherical active zone is preferable to focus the energy on generally spherical tissue targets. Wavelength elongation causes the electromagnetic field to stretch down along the length of the device toward the generator, resulting in a generally comet- or "hot-dog"-shaped active zone.

Wavelength elongation can be significantly reduced in medical microwave antennas by dielectrically buffering the antenna geometry with a material having an unchanging dielectric constant, as described in U.S. application Ser. Nos. 13/835,283 and 13/836,519, the disclosure of each of which are incorporated by reference herein. The material of unchanging dielectric constant surrounds the antenna, reducing the influence of the tissue electrical properties on antenna wavelength. By controlling wavelength elongation through dielectric buffering, the antenna impedance match and field shape can be maintained, enabling a large active ablation zone with a predetermined and robust shape.

By providing dielectric buffering with a circulated fluid, such as with saline or water, the high dielectric constants of these materials can be leveraged in the antenna geometry design, and furthermore the circulated fluid can be used to simultaneously cool the microwave components, including the coaxial feed line and antenna. Cooling of the microwave components also enables higher power handling of the components which can be used to deliver more energy to the antenna to create larger active zones.

As described above, the shape of the active zone about an antenna is determined, in part, by the geometry of the antenna. Ordinary ablation antennas do not utilize antenna geometry in combination with wavelength buffering to effectively control microwave field shape. These antennas do not create spherical active zone shapes nor are the active zones robust and unchanging across tissue types or during tissue heating. These antennas allow microwave energy to spread along the external conductor of the device from the device tip towards the generator. The spreading of microwave energy along the shaft results in comet- or "hot-dog"-shaped active zones.

Microwave antennas can be equipped with a choke or balun, a component of the antenna geometry that improves impedance matching and also can aid in focusing microwave energy into a predetermined shape. When combined with wavelength buffering, a balun or choke can effectively block the backwards propagation of electromagnetic waves along the external conductor toward the generator across various tissue types and during tissue heating, focusing the energy into a robust spherical active zone.

One implementation of a balun includes a balun dielectric that is disposed on the outer conductor of a coaxial cable and an outer balun conductor disposed on the balun dielectric. The balun creates a short section of coaxial waveguide arranged about the inner coaxial cable where the outer conductor of the coaxial cable is the inner conductor of the balun. The balun is disposed about the coaxial cable near the feed of the antenna and in one implementation has a length of $\lambda/4$ where $\lambda$ is the wavelength of the electromagnetic wave within the balun. The balun outer conductor and inner conductor are shorted together at the proximal end to create a $\lambda/4$ short-circuited balun.

One way of describing the function of a $\lambda/4$ short-circuited balun is as follows: an electromagnetic wave propagates proximally along the radiating section of the antenna, enters the balun, reflects off of the short-circuited proximal end of the balun, propagates forward to the distal end of the balun, and exits the balun back onto the antenna radiating section. With this arrangement of balun length, when the electromagnetic wave reaches the distal end of the balun and travels back onto the antenna radiating section, the electromagnetic wave has accumulated a full $\lambda$ of phase change. This is due to the $\lambda/4$ distance traveled forward within the balun, the $\lambda/4$ distance traveled backward within the balun and a $\lambda/2$ phase change which occurs with the reflection off of the short-circuited proximal end of the balun. The result is an electromagnetic wave which, rather than propagating along the external surface of the cable toward the generator, is a wave which is redirected back toward the distal tip of the antenna in coherent phase with the other waves on the antenna radiating section.

The balun, however, substantially increases the diameter of the microwave antenna as well as the needle through which the microwave antenna passes. The size of the needle may limit the uses for the microwave antenna in minimally-invasive procedures, especially when there are repeated treatments.

SUMMARY

In one aspect, the present disclosure features a microwave ablation applicator. The microwave ablation applicator includes a feed-line segment, a step-down segment, and a radiator base segment. The feed-line segment includes a first inner conductor, a first dielectric disposed on the outer surface of the first inner conductor and having a first face in a plane perpendicular to the longitudinal axis of the first inner conductor, and a first outer conductor disposed on the outer surface of the first dielectric. The step-down segment includes a second inner conductor, a second dielectric having a diameter less than the diameter of the first dielectric and disposed on the outer surface of the second inner conductor, and a second outer conductor disposed on the outer surface of the second dielectric.

The radiator base segment includes a third inner conductor, a third dielectric having a diameter less than the diameter of the first dielectric and disposed on the outer surface of the third inner conductor, a third outer conductor disposed on the outer surface of the proximal end of the third dielectric so as to form a feed gap at a distal end of the radiator base segment, a balun dielectric disposed on the outer surface of the third outer conductor, and a balun outer conductor disposed on the outer surface of the balun dielectric. The third outer conductor has a length that is less than the length of the third dielectric so as to leave a feed gap.

One or more of the feed-line segment, the step-down segment, and the radiator base segment may be rigid, semi-rigid, or flexible. The diameter of the second and third inner conductors may be equal to the diameter of the first inner conductor. The second and third inner conductors may be an extension of the first inner conductor. The outer diameter of the balun conductor may be equal to the outer diameter of the first outer conductor of the feed-line segment.

The step-down segment may taper from a first diameter at proximal end of the step-down segment to a second smaller diameter at a distal end of the step-down segment. The step-down segment may include multiple steps. A ferrule may be disposed at each of the steps of the step-down segment. The length of the step-down segment may be scaled by the dielectric constant of the second dielectric.

The feed-line segment, the step-down segment, and the radiator base segment are machined from a coaxial feed-line core may include an inner conductor and a dielectric insulator disposed around the inner conductor.

At least one of the first dielectric, the second dielectric, the third dielectric, and the balun dielectric may be dielectric tape. The second dielectric may be a foamed PTFE, low-density PTFE (LDPTFE), microporous PTFE, tape-wrapped PTFE, tape-wrapped and sintered PTFE, or PFA. The second outer conductor may be a silver-plated copper flat-wire braid, a solid-drawn copper tube, a conductive ink-coated PET heat shrink, a silver-coated PET heat shrink, or a silver-plated copper-clad steel braid.

In another aspect, the present disclosure features a microwave ablation applicator. The microwave ablation applicator includes a coaxial feed-line segment, an impedance step-down segment, a radiator base segment, and a coaxial balun disposed on the radiator base segment. The microwave ablation applicator also includes a radiating section attached to a distal end of the radiator base segment, and a dielectric buffering and cooling segment configured to receive the coaxial feed-line segment, the impedance step-down segment, the radiator base segment, and the radiating section.

One or more of the feed-line segment, the step-down segment, and the radiator base segment may be rigid, semi-rigid, or flexible. The outer diameter of the coaxial balun may be equal to or approximately equal to the outer diameter of the coaxial feed-line segment.

The dielectric buffering and cooling segment may include a first tube and a second tube disposed within the first tube. The second tube defines an outflow conduit between the inner surface of the first tube and the outer surface of the second tube, and defines an inflow conduit between the inner surface of the second tube and the outer surfaces of the coaxial cable and attached radiating section. The dielectric buffering and cooling segment may include a first tube defining inflow and outflow conduits for carrying cooling fluid.

BRIEF DESCRIPTION OF THE DRAWINGS

Objects and features of the presently disclosed energy-delivery devices with a fluid-cooled probe assembly and systems including the same will become apparent to those of ordinary skill in the art when descriptions of various embodiments thereof are read with reference to the accompanying drawings, of which:

FIG. 2A is a perspective view of the microwave applicator of the microwave ablation system of FIG. 1 in accordance with aspects of the present disclosure;

FIG. 2B is a longitudinal, cross-sectional view of the microwave applicator of FIG. 2A;

FIG. 2C is a transverse, cross-sectional view of the microwave applicator of FIG. 2A in accordance with an aspect of the present disclosure;

FIG. 2D is a transverse, cross-sectional view of the microwave applicator of FIG. 2A in accordance with another aspect of the present disclosure;

DETAILED DESCRIPTION

Figure 1:
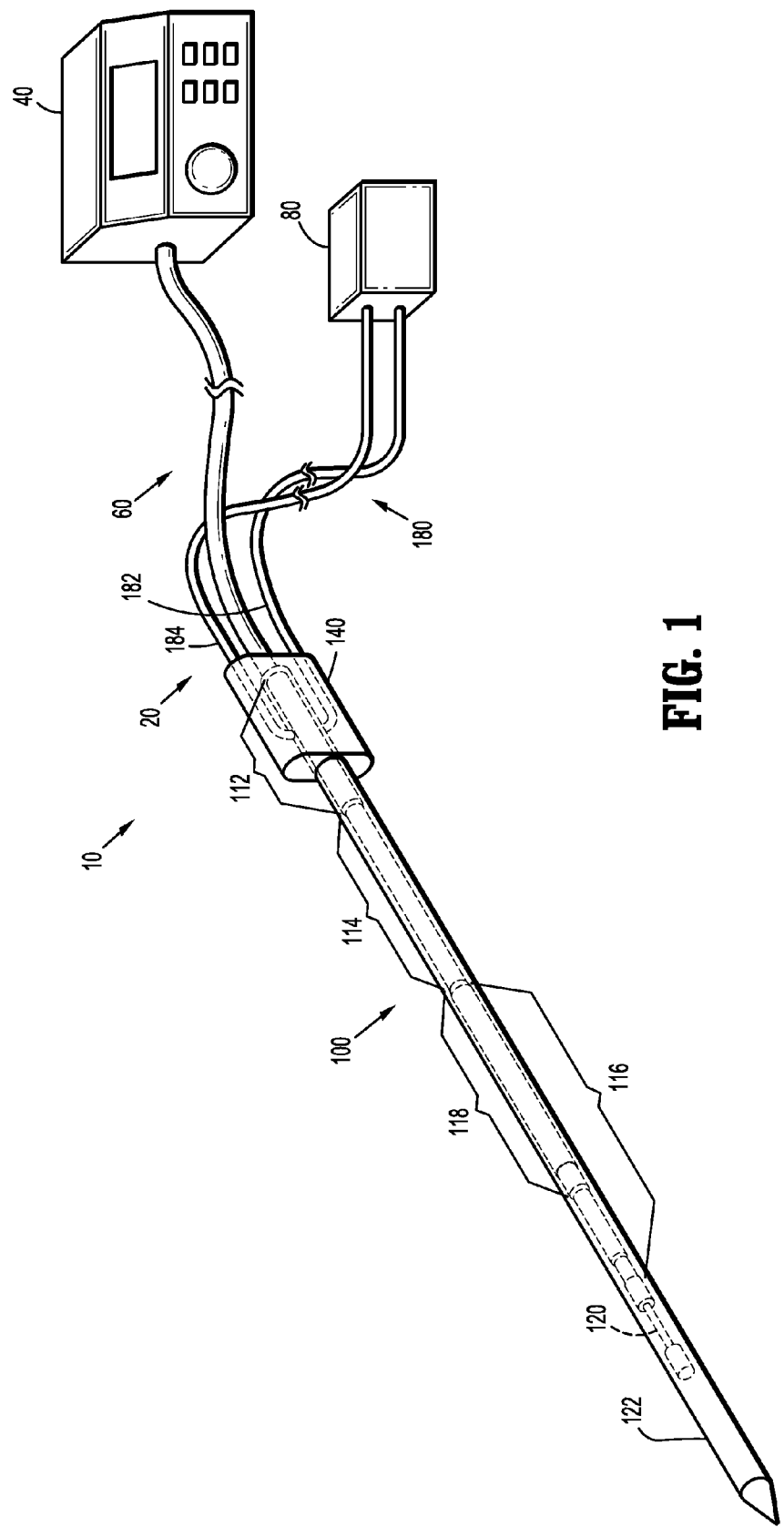
FIG. 1 is a block diagram of a microwave ablation system in accordance with aspects of the present disclosure.

The balun has the largest radial dimensions along the length of the microwave applicator. The present disclosure is generally directed to microwave ablation applicators and methods of manufacturing microwave ablation applicators having small radial dimensions. This is accomplished by reducing the radial dimensions of the landing on which the balun is built.

According to the present disclosure, the diameter of the antenna geometry may be reduced to be less than or equal to or approximately equal to the diameter of the coaxial feed-line. The miniaturization of the antenna geometry provides at least the following advantages: (1) it reduces the overall radial size of the microwave applicator without significantly compromising ablation performance or device strength; (2) it enables use of a larger coaxial cable feed-line, which reduces energy loss in the coaxial cable feed-line and thus increases energy delivery to the radiator; (3) it provides additional space within the microwave applicator without increasing overall radial size for various structures and features of the microwave applicator, such as the fluid channels, strengthening members, and centering features or sensors; and (4) it enables various manufacturing techniques, such as sliding the fully assembled microwave components into a multi-lumen catheter from one end, which would otherwise not be possible because of inconsistent radial dimensions between the microwave coaxial cable and the antenna.

With respect to endobronchial ablation, the miniaturization of the microwave applicator enables the technical feasibility (e.g., required tissue effect and appropriateness of the cooling) of a saline or water dielectric buffered and electrically choked (via the balun) microwave radiator at a 2.8 mm bronchoscope channel size. This further improves the tissue effect and cooling performance of the same application sized up to a 3.2 mm bronchoscope channel size device. Other intravascular, percutaneous, surgical, and laparoscopic applications where catheter size (French sizing) is of clinical significance are envisioned to benefit similarly. This may also provide space within the microwave applicator assemblies for thermocouple temperature sensors, which are described in U.S. application Ser. Nos. 13/836,519 and 13/924,277, the disclosure of each of which are incorporated by reference herein. Additionally, by maintaining a line-to-line dimension between the diameter of the feed-line coaxial segment and the diameter of the antenna geometry (including a balun), the microwave applicator assembly may be slid into a closed out (tipped) lumen from the proximal end, thus simplifying the manufacturing process. The manufacturing methods of the present disclosure may be used in the miniaturization and strengthening of ablation needles.

Embodiments of the microwave ablation systems and components are described with reference to the accompanying drawings. Like reference numerals may refer to similar or identical elements throughout the description of the figures. As shown in the drawings and as used in this description, the term "proximal" refers to that portion of the apparatus, or component of the apparatus, closer to the user and the term "distal" refers to that portion of the apparatus, or a component of the apparatus, farther from the user.

This description may use the phrases "in an embodiment," "in embodiments," "in some embodiments," or "in other embodiments," which may each refer to one or more of the same or different embodiments in accordance with the present disclosure.

As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection. As it is used in this description, "transmission line" generally refers to any transmission medium that can be used for the propagation of signals from one point to another. As it is used in this description, "fluid" generally refers to a liquid, a gas, or both.

FIG. 1 is a block diagram of a microwave tissue treatment system 10 in accordance with aspects of the present disclosure. The microwave tissue treatment system 10 includes a microwave tissue treatment device 20 having a microwave applicator or antenna assembly 100 connected to a microwave generator 40 through a feedline 60. The microwave tissue treatment device 20 may include one or more pumps 80, e.g., a peristaltic pump or the like, for circulating a cooling or heat dissipative fluid through the microwave applicator or antenna assembly 100 via an inflow fluid conduit 182 and an outflow fluid conduit 184 of a cooling system 180. The mechanical functionality of the pump in driving fluid through the system may be substituted by driving the fluid with pressurized and regulated reservoirs.

The feedline 60 may range in length from about 7 feet to about 10 feet, but may be either substantially longer or shorter if required in a particular application. The feedline 60 transfers microwave energy to microwave tissue treatment device 20. The feedline 60 includes a coaxial cable having an inner conductor, an outer conductor, and a dielectric interposed between the inner and outer conductors. The dielectric electrically separates and/or isolates the inner conductor from the outer conductor. The feedline 60 may further include any sleeve, tube, jacket, or the like formed of any conductive or non-conductive material. The feedline 60 may be separable from, and connectable to, the antenna assembly 100 or the microwave tissue treatment device 20.

The inner and outer conductors are each formed, at least in part, of a conductive material or metal, such as stainless steel, copper, or gold. In certain embodiments, the inner and outer conductors of feedline 60 may include a conductive or non-conductive substrate that is plated or coated with a suitable conductive material. The dielectric may be formed of a material having a dielectric value and tangential loss constant of sufficient value to electrically separate and/or isolate the respective inner and outer conductors from one another, including but not being limited to, expanded foam polytetrafluoroethylene (PTFE), polymide, silicon dioxide, or fluoropolymer. The dielectric may be formed of any non-conductive material capable of maintaining the desired impedance value and electrical configuration between the respective inner and outer conductors. In addition, the dielectric may be formed from a combination of dielectric materials.

The antenna assembly 100 of the microwave tissue treatment system 10 includes a coaxial feed-line segment 112, a impedance step-down segment 114, a radiator base segment 116 on which a choke or coaxial balun 118 is disposed, a distal radiating section 120, and a dielectric buffering and cooling structure 122.

The proximal portion of the antenna assembly 100 may include a connecting hub 140. The connecting hub 140 defines a conduit configured and dimensioned to receive a distal end of the feedline 60, additional conduits configured and dimensioned to receive the inflow conduit 182 and the outflow conduit 184 of the cooling system 180, and one or more apertures formed in an internal surface of the connecting hub 160 that are configured and dimensioned to receive the inflow conduit 182 and the outflow conduit 184, respectively. Connecting hub 160 may be formed of any suitable material including, but not limited to, polymeric materials. Although not explicitly shown, the hub may also include conduits configured and dimensioned to receive sensors, including but not limited to thermocouples or impedance monitoring electrodes.

As described above, the microwave ablation applicator of the present disclosure minimizes the radial dimension of a coaxial-fed microwave ablation applicator. Specifically the radial dimension of the balun, which is largest radial dimension along the microwave ablation radiator, is minimized. This may be accomplished by reducing the dimension of the landing on which the balun is built.

As shown in FIG. 1, the microwave ablation applicator includes six segments or structures: (1) the coaxial feed-line segment 112 of the coaxial cable, (2) the impedance step-down segment 114 of the coaxial cable, (3) the radiator base segment 116 of the coaxial cable, (4) the coaxial balun 118, (5) the distal radiating section 120, and (6) the dielectric buffering and cooling structure 122, which includes conduits for carrying dielectric buffering and cooling fluid through the microwave applicator to dielectrically buffer and cool at least the radiator base segment 116 and distal radiating section 120. The construction of and the materials used for each of these segments or structures will now be described.

FIGS. 2A-2D show the microwave applicator inserted into the dielectric buffering and cooling structure 122. The coaxial feed-line segment 112 (FIG. 1) may be constructed of a coaxial cable of any variety, including a rigid, semi-rigid, or flexible coaxial cable. The impedance of the waveguide formed by the coaxial cable may be 50 ohms, but may range from 20 ohms to 150 ohms. An inner conductor 212 of the coaxial feed-line segment 112 is surrounded by a dielectric insulator 214, which, in turn, is partially or fully covered by an outer conductor 216 (also referred to as a shield). For a 150 Watt, 2450 MHz design, for example, the inner conductor 212 may have a diameter of 0.02870 cm, the dielectric insulator 214 may have a diameter of 0.09144 cm, and the outer conductor 216 may have a diameter of 0.1054 cm.

The inner conductor 212 may be a silver-plated solid copper wire. The dielectric insulator 214 may be an extruded polytetrafluoroethylene (PTFE) dielectric insulator, wrapped PTFE, foamed PTFE, or perfluoroalkoxy (PFA). The outer conductor 216 may be a silver-plated copper wire braid constructed from either flat or round braid wire. A jacket (not shown) for environmental and mechanical robustness may be applied onto or melted into the braided shield. The jacket may be a heat shrink material, such as polyethylene terephthalate (PET) or fluorinated ethylene propylene (FEP), or an extruded thermoplastic.

The impedance step-down segment 114 may include an inner conductor 222 that is the same as the inner conductor 212 of the coaxial feed-line segment 112. Thus, the inner conductor 222 may be unchanged and seamless between the coaxial feed-line segment 112 and the impedance step-down segment 114 to simplify manufacture of the microwave applicator and improve electrical performance. In other words, the inner conductor 222 may be an extension of the inner conductor 212. In embodiments, the radial dimension of the inner conductor 222 may be reduced. The difference between the coaxial feed-line segment 112 and the impedance step-down segment 114 is that the outer radial dimension of the impedance step-down segment 114 is reduced according to the calculations described below.

The length of the impedance step-down segment 114 may be optimized for electrical performance at one quarter of the wavelength of the frequency of operation. The length of the impedance step-down segment 114 may be scaled by the dielectric constant of the impedance step-down segment's dielectric insulator 224. For example, the length of the impedance step-down segment 114 may be 2.1 cm for an operation frequency of 2450 MHz. In other embodiments, the length of the impedance step-down segment 114 may deviate from a quarter wavelength. For example, the length of the impedance step-down segment 114 may be 5.6 cm for an operation frequency of 915 MHz and 0.9 cm for 5800 MHz. In yet other embodiments, the impedance step-down segment 114 may be stepped down using a variety of approaches including a taper step down (described in more detail below), a multiple segment step down (also described in more detail below), or an exponential tapering.

The impedance step-down segment 114 may be constructed from the same materials as the coaxial feed-line segment 112, or the impedance step-down segment 114 may use a different combination of materials than the coaxial feed-line segment 112. The dielectric insulator 224 may be a foamed PTFE, such as low-density PTFE (LDPTFE) or microporous PTFE, tape-wrapped PTFE, tape-wrapped and sintered PTFE, or PFA. The outer conductor 226 may be a silver-plated copper flat wire braid, a solid-drawn copper tube, a conductive ink-coated PET heat shrink (e.g., silver ink-coated PET heat shrink), or a silver-plated copper-clad steel braid.

The radiator base segment 116 may include an inner conductor 232 that is unchanged and seamless with the inner conductor 222 of the impedance step-down segment 114 and the inner conductor 212 of the coaxial feed-line segment 112, which would simplify manufacture of the radiator base segment 116 and would improve electrical performance. If the inner conductor 232 of the radiator base segment 116 were to change with the radiator base segment 116, its radial dimension may be reduced. A difference between the radiator base segment 116 and the impedance step-down segment 114 is that the radial dimension of the radiator base segment's dielectric insulator 234 is reduced according to the calculations described below.

The far distal end of the outer conductor or shield 236 of the radiator base segment 116 is removed to create the feed gap 238, which allows microwave fields to propagate onto the distal radiating section 120 from the coaxial waveguide.

The length of the radiator base segment 116 is approximately equal to the sum of the lengths of the coaxial balun 118, the feed gap 238, and the proximal radiating arm, which is the length between the coaxial balun 118 and the feed gap 238. For example, for an operating frequency of 2450 MHz, the coaxial balun 118 may have a length of 2 cm, the proximal radiating arm may have a length of 1 cm, and the feed gap 238 may have a length of 0.3 cm.

The radiator base segment 116 may be constructed from the same materials as or different materials from the coaxial feed-line segment 112 and/or the impedance step-down segment 114. The dielectric insulator 234 of the radiator base segment 116 may be a low-density PTFE (e.g., a foamed PTFE), a tape-wrapped PTFE, a tape-wrapped and sintered PTFE, or a PFA. The outer conductor 236 may be a silver-plated copper flat-wire braid, a solid-drawn copper tube, a silver ink-coated PET heat shrink, or a silver-plated copper-clad steel braid.

The coaxial balun 118 is assembled on top of the radiator base segment as shown in FIGS. 2B-2D. The coaxial balun 118 is composed of a balun dielectric insulator 244 and a balun outer conductor 246 (also referred to as a balun shield).

The overall outer diameter of the coaxial balun 118 may be set equal to or approximately equal to the overall outer diameter of the coaxial feed-line segment 112, such that the largest overall radial dimension of the device is not increased by the coaxial balun 118. For example, the overall outer diameter of the coaxial balun 118 may be 0.105 cm. This equality sets the initial conditions of the design calculations described below. The length of the coaxial balun 118 is equal to one quarter of the wavelength of the frequency of operation, which is scaled by the dielectric constant of the balun dielectric insulator 244. For example, the length of the coaxial balun 118 may be 2.0 cm in length for operation at 2450 MHz. The balun dielectric insulator 244 may extend beyond the distal end of the coaxial balun outer conductor or shield 246, as shown in FIG. 2B (insulator extension 248), which enhances the effectiveness of the coaxial balun 118 across a variety of physiological conditions. For example, the length of the extended balun dielectric insulator 244 may be 0.3 cm.

The coaxial balun 118 may be constructed from the same materials as the coaxial feed-line segment 112, or may vary from the specific materials of the coaxial feed-line segment 112. For example, the coaxial dielectric insulator 244 may be a foamed PTFE (LDPTFE), tape-wrapped PTFE, tape-wrapped and sintered PTFE, or PFA. The balun outer conductor 246 may be a silver-plated copper flat-wire braid, a solid-drawn copper tube, a silver ink-coated PET heat shrink, or a silver-plated copper-clad steel braid.

The distal radiating section 120 is an elongated conductor which is soldered, crimped, or welded onto the distal end of the inner conductor 232 of the radiator base segment 116. The shape of the distal radiating section 120 may be a cylinder. Alternatively, the distal radiating section 120 may be composed of several cylinders of varying diameter, such as a barbell or pin with a widened base. Additional heat-sinking features, such as burs and fins, may be added to the distal radiating section 120 to increase the radiating effectiveness of the microwave applicator. These features, such as the barbell mentioned above, may also help to center the radiator within the dielectric buffering and cooling structure 122.

The length of the distal radiating section 120 may be designed for approximately one quarter wavelength at the frequency of operation. For example, the length of the distal radiating section 120 may be approximately 1 cm for an operation frequency of 2450 MHz. Alternatively, the distal radiating section 120 may be reduced or lengthened to match the line impedance of the radiator base segment 116 to the overall antenna impedance. Increasing or decreasing the length of the distal radiating section 120 proportionally reduces or increases, respectively, the length of the proximal radiating arm, maintaining the overall length of the antenna at half wavelength resonance at the frequency of operation. For example, the total length of the distal radiating section 120, including the feed gap 238, may be approximately 2.3 cm for operation at 2450 MHz.

The distal radiating section 120 may be gold-plated brass, silver-plated copper, or any other composite of materials having high surface conductivity, such as a polymer rod with conductive coating. The distal radiating section 120 may also be created by extending the radiator base segment's dielectric insulator 234 and inner conductor 232 an appropriate length and covering with a conductive surface, such as electroplating, conductive ink, wrapped foil, or braided wire.

The dielectric buffering and cooling structure 122 includes a mechanical support for the device, circulated cooling fluid, such as gas or liquid, and chambers to enable the circulation of the fluid, such as concentric inflow and outflow tubes 202 and 203 forming fluid paths 208 and 206, respectively, or multi-lumen thermo-plastic extrusion, e.g., lumens 204-207. The dielectric buffering of the antenna from the surrounding tissue environment is provided by the circulated liquid extending over the length of the radiating section. Alternatively, the cooling lumens and fluids may terminate proximal to the distal radiating section 120 and high dielectric solid material may be disposed distally over the radiating section of the microwave applicator to dielectrically buffer the antenna and provide mechanical stiffness.

The dielectric buffering and cooling structure 122 may be composed of various thermoplastics and may be manufactured according to a multi-lumen extrusion approach. The dielectric buffering and cooling structure 122 may include an outflow tube 203 composed of fiber glass and an inflow tube 202 composed of polyimide or PET extrusion and may be manufactured according to a concentric approach, in which materials are layered upon each other. The inflow tube 202 and the outflow tube 203 may alternatively be composed of a Kevlar braid thermoplastic composite. The cooling fluid may be water, saline, or any common water-based liquid. The high dielectric solid material may be a ceramic material, such as Yttria Tetragonal Zirconia Polycrystal (YTZP).

In embodiments, the microwave ablation applicator may be designed by first optimizing the step-down dielectric design. One example approach to determining the dimensions of the feed-line segment, the step-down segment, and the radiator base segment of the microwave ablation applicator is to constrain the outer diameter of the balun to the outer diameter of the feed-line so that the outer diameter of the microwave ablation applicator assembly is no larger than the outer diameter of the feed-line. The lengths and diameters of each segment may also be designed to achieve low insertion loss through the antenna feed gap at a frequency of operation. The frequency of operation may be a bandwidth of operation, such as from 2400 MHz to 2500 MHz. After determining the dimensions of the segments of the microwave ablation applicator, the distal radiating section, balun, and dielectric buffering and cooling structures are added to the design, and the dimensions of the segments are then further optimized to achieve a controlled energy pattern and high energy-to-tissue efficiency.

The dimensions of the segments of the microwave ablation probe may be determined by starting with the target balun radial dimensions, which may be chosen to be approximately equal to or smaller than the radial dimensions of the coaxial feed-line segment 112. Next, the dimensions of the radiator base segment 116 are determined, and then the dimensions of the step-down segment 114 are determined using a quarter-wave matching equation. The quarter-wave matching equation matches the impedance change between the larger coaxial feed-line segment 112 and the smaller radiator base segment 116. This method of determining the dimensions of the segments of the microwave ablation probe is illustrated by the following example.

First, the dimensions of the coaxial feed-line segment 112 are calculated. The diameter of the inner conductor 212 ($IC_1$) of the coaxial feed-line segment 112 is calculated as follows:

$$IC_1 = e^{-Z_{feed}\sqrt{\varepsilon_{r1}} \cdot 2\pi\sqrt{\varepsilon_0/\mu_0} + \log(OD_{dielectric1})}, \quad (1)$$

where $Z_{feed}$ is the impedance of the coaxial feed-line segment 112, $\varepsilon_{r1}$ is the dielectric constant of the dielectric insulator 214 of the coaxial feed-line segment 112, $\varepsilon_0$ is the permittivity of free space or vacuum, $\mu_0$ is the permeability of vacuum, and $OD_{delectric1}$ is the outer diameter of the dielectric insulator 214. Equation (1) is derived from the equation for the impedance of a coaxial cable. The total or outer diameter of the coaxial feed-line segment 112 ($OD_{cable_1}$) is calculated as follows:

$$OD_{cable_1} = OD_{dielectric_1} + ODadd_{braid_1} + ODadd_{jacket_1} \quad (2)$$

where $ODadd_{braid_1}$ is the diameter addition from the outer conductor 216 and $ODadd_{jacket_1}$ is the diameter addition from the jacket of the coaxial feed-line segment 112.

The dimensions of the coaxial balun 118 may be calculated by setting the outer diameter of the balun structure or choke ($OD_{choke}$) equal to the outer diameter of the coaxial feed-line segment 112 ($OD_{cable_1}$), which may be expressed by the following equation:

$$OD_{choke} = OD_{cable_1} \quad (3)$$

In other embodiments, the outer diameter of the choke ($OD_{choke}$) may be set less than the outer diameter of the coaxial feed-line segment 112 ($OD_{cable_1}$). The outer diameter of the choke's dielectric insulator 244 ($OD_{choke\ dielectric}$) is then determined from the following equation:

$$OD_{choke\ dielectric} = OD_{choke} - ODadd_{choke\ jacket} - ODadd_{choke\ braid}, \quad (4)$$

where $ODadd_{choke\ jacket}$ is the diameter addition from the choke's jacket and $ODadd_{choke\ braid}$ is the diameter addition from the outer conductor 246 of the choke or coaxial balun 118. The inner diameter of the balun insulator 244 ($ID_{choke\ dielectric}$) is then determined from the following equation:

$$ID_{choke\ dielectric} = OD_{choke\ dielectric} - OD_{choke\ dielectric} \quad (5)$$

Next, the dimensions of the radiator base segment 116 are calculated. First, the diameter of the inner conductor 232 of the radiator base segment 116 ($IC_3$) is set equal to the diameter of the inner conductor 212 ($IC_1$) of the coaxial feed-line segment 112 ($IC_1$), that is:

$$IC_3 = IC_1 \quad (6)$$

The outer diameter of the radiator base segment's insulator 234 ($OD_{dielectric_3}$) is then calculated as follows:

$$OD_{dielectric_3} = ID_{choke\ dielectric} - ODadd_{braid_3} - ODadd_{jacket_3} \quad (7)$$

where $ODadd_{braid_3}$ is the diameter addition from the outer conductor 246 of the choke or coaxial balun 118 and $ODadd_{jacket_3}$ is the diameter addition from the choke's jacket.

Then, the inner diameter of the radiator base segment's insulator 234 ($ID_{dielectric_3}$) is set equal to the diameter of the inner conductor 232 of the radiator base segment 116 ($IC_3$), that is:

$$ID_{dielectric_3} = IC_3 \quad (8)$$

The outer diameter of the cable for the radiator base segment 234 ($OD_{cable_3}$) is then calculated according to the following equation:

$$OD_{cable_3} = OD_{dielectric_3} + ODadd_{braid_3} + ODadd_{jacket_3} \quad (9)$$

Next, the step-down impedance is calculated by first calculating the feed-line and radiator base segment impedances. The impedance of the coaxial feed-line segment 112 is given by the equation:

$$Z_{cable_1} = \frac{\log(OD_{dielectric_1}/IC_1)}{2\pi\sqrt{\mu_0/(\varepsilon_0 \cdot \varepsilon_{r_1})}} \quad (10)$$

The impedance of the radiator base segment 116 is given by the equation:

$$Z_{cable_3} = \frac{\log(OD_{dielectric_3}/IC_3)}{2\pi\sqrt{\mu_0/(\varepsilon_0 \cdot \varepsilon_{r_3})}} \quad (11)$$

where $\varepsilon_{r3}$ is the dielectric constant of the dielectric insulator 234 of the radiator base segment 116.

The impedance of the step-down segment 114 may be calculated using the quarter wave impedance transformer approach by taking the square root of the product of the impedances of the coaxial feed-line segment 112 (9) and radiator base segment 116 (10) as shown in the following equation:

$$Z_{cable_2} = \sqrt{Z_{cable_1} Z_{cable_3}} \quad (12)$$

The dimensions of the step-down segment 114 may then be calculated as follows. The diameter of the inner conductor 222 of the step-down segment 114 is set equal to the diameter of the inner conductor 212 of the coaxial feed-line segment 112, that is:

$$IC_2 = IC_1 \quad (13)$$

Then, the outer diameter of the step-down segment's insulator 224 ($OD_{dielectric_2}$) is calculated using the following equation:

$$OD_{dielectric_2} = e^{Z_{cable_2}\sqrt{\varepsilon_{r2}} \cdot 2\pi\sqrt{\varepsilon_0/\mu_0} + \log(IC_2)}, \quad (14)$$

where $\varepsilon_{r_2}$ is the dielectric constant of the dielectric insulator 224 of the step-down segment 114. Equation (14) is derived from the impedance of the coaxial cable equation.

The inner diameter of the step-down segment's insulator 224 is given by the following equation:

$$ID_{dielectric_3} = IC_3 \quad (15)$$

Then, the total outer diameter of the step-down segment 114 is calculated according to the equation:

$$OD_{cable_2} = OD_{dielectric_2} + ODadd_{braid_1} + ODadd_{jacket_1} \quad (16)$$

Figure 3A:
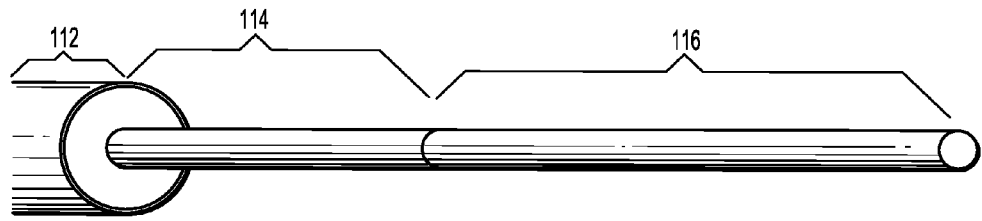
FIG. 3A is a perspective view of a coaxial cable assembly after performing a step of a method of manufacturing the microwave applicator of FIGS. 2A-2D in accordance with aspects of the present disclosure.
Figure 3B:
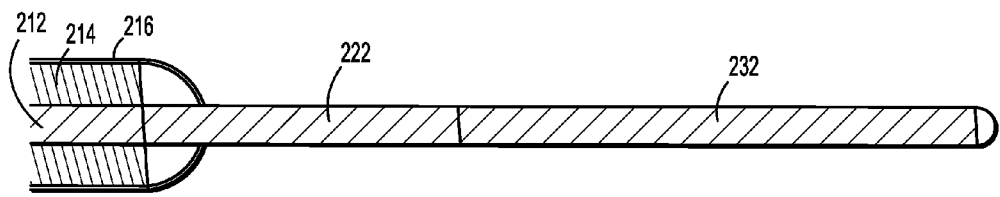
FIG. 3B is a longitudinal, cross-sectional view of the coaxial cable assembly of FIG. 3A.

Using the dimensions determined from the design of the microwave ablation applicator described above, the microwave ablation applicator may be manufactured according to a variety of methods, examples of which are described below. For example, FIGS. 3A-10B illustrate a method for manufacturing the microwave applicator by stacking dielectric cylinders. As shown in FIGS. 3A and 3B, the manufacturing method begins with a coaxial feed-line segment having a first inner conductor 212, a first insulator 214, and an outer conductor 216; an impedance step-down segment 114 having a second inner conductor 222; and a radiator base segment 232 having a third inner conductor. This configuration may be formed by stripping the insulator and outer conductor from a distal portion of a coaxial cable.

Figure 4A:
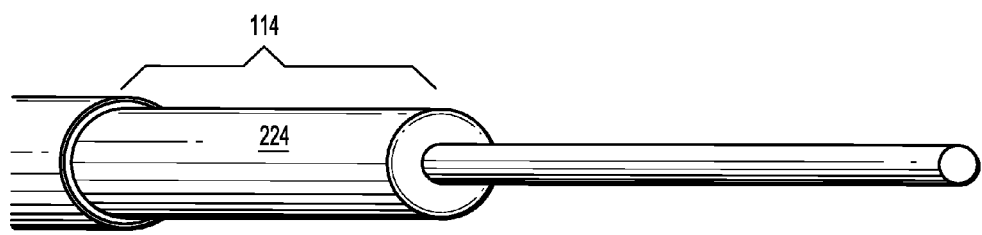
FIG. 4A is a perspective view of a coaxial cable assembly after performing another step of the method of manufacturing the microwave applicator of FIGS. 2A-2D.
Figure 4B:
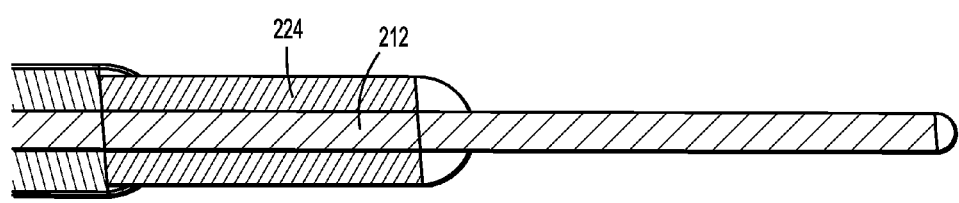
FIG. 4B is a longitudinal, cross-sectional view of the coaxial cable assembly of FIG. 4A.
Figure 5A:
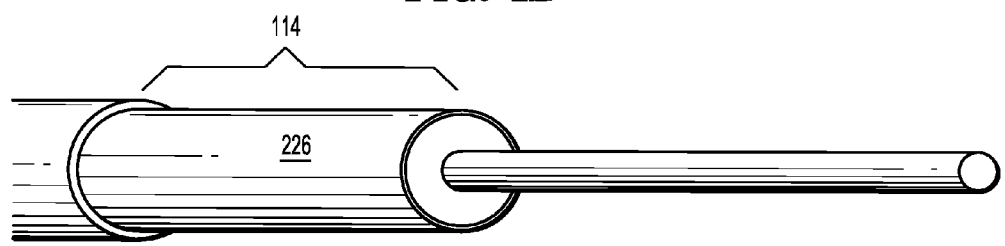
FIG. 5A is a perspective view of a coaxial cable assembly after performing still another step of the method of manufacturing the microwave applicator of FIGS. 2A-2D.
Figure 5B:
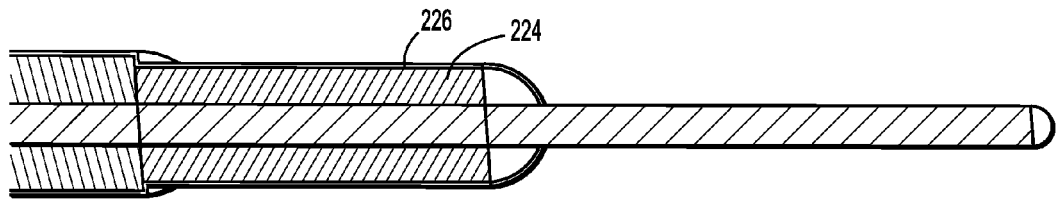
FIG. 5B is a longitudinal, cross-sectional view of the coaxial cable assembly of FIG. 5A.

Next, as shown in FIGS. 4A and 4B, a second insulator 224 having a diameter less than the diameter of the first insulator 214 is disposed around the second inner conductor 222 of the impedance step-down segment 114. This may be accomplished by sliding a cylindrical insulator onto the second inner conductor 222. Next, as shown in FIGS. 5A and 5B, an outer conductor 226 is disposed on the surface of the second insulator 224 of the impedance step-down segment 114.

Figure 6A:
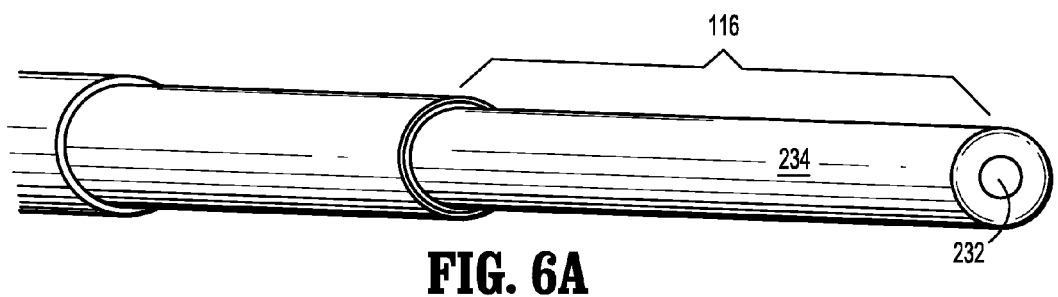
FIG. 6A is a perspective view of a coaxial cable assembly after performing still another step of the method of manufacturing the microwave applicator of FIGS. 2A-2D.
Figure 6B:
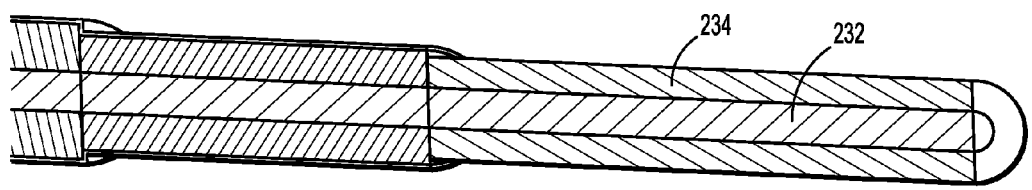
FIG. 6B is a longitudinal, cross-sectional view of the coaxial cable assembly of FIG. 6A.
Figure 7A:
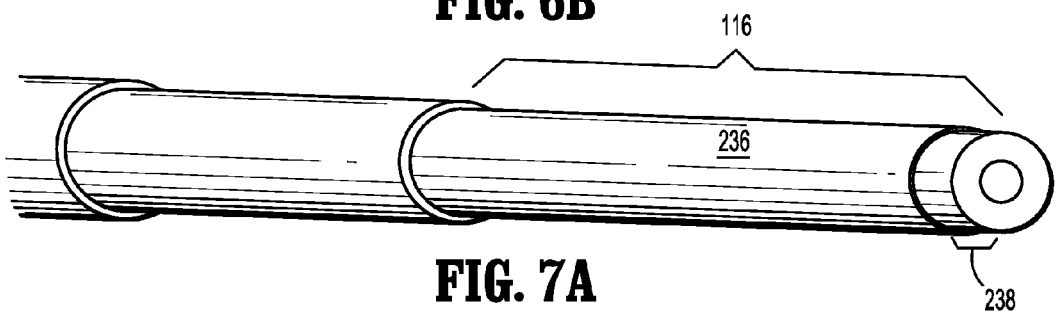
FIG. 7A is a perspective view of a coaxial cable assembly after performing still another step of the method of manufacturing the microwave applicator of FIGS. 2A-2D.
Figure 7B:
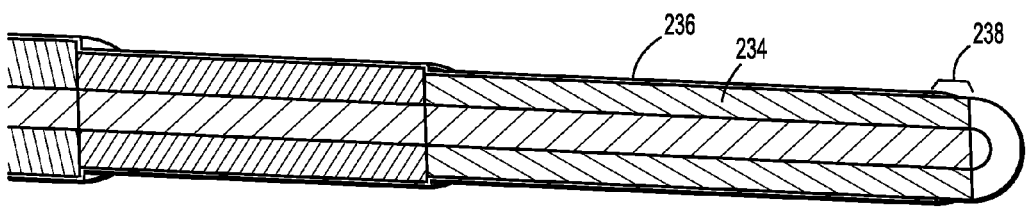
FIG. 7B is a longitudinal, cross-sectional view of the coaxial cable assembly of FIG. 7A.

In the next step of the manufacturing method, a third insulator 234 having a diameter less than the diameters of the first insulator 214 and the second insulator 224 is disposed around the third inner conductor 232 of the radiator base segment 116, as shown in FIGS. 6A and 6B. This may be also accomplished by sliding a cylindrical insulator onto the third inner conductor 232. Next, as shown in FIGS. 7A and 7B, an outer conductor 236 is disposed on the surface of a proximal portion of the third insulator 234 of the radiator base segment 116 leaving a distal portion of the third insulator 234 exposed to form a feed gap 238.

Figure 8A:
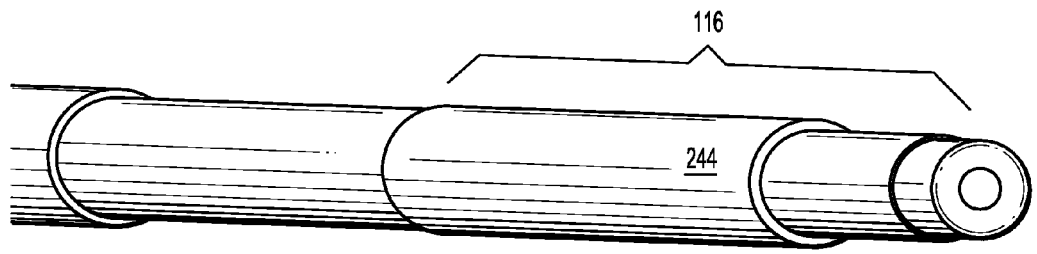
FIG. 8A is a perspective view of a coaxial cable assembly after performing still another step of the method of manufacturing the microwave applicator of FIGS. 2A-2D.
Figure 8B:
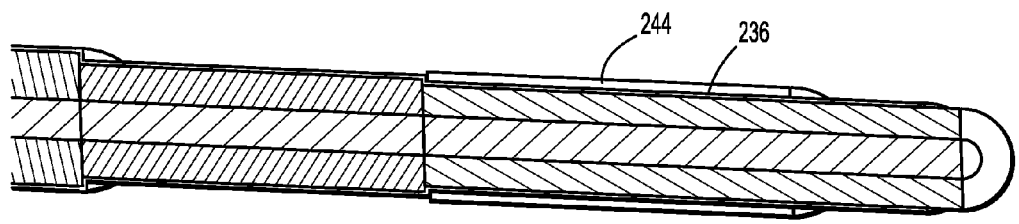
FIG. 8B is a longitudinal, cross-sectional view of the coaxial cable assembly of FIG. 8A.
Figure 9A:
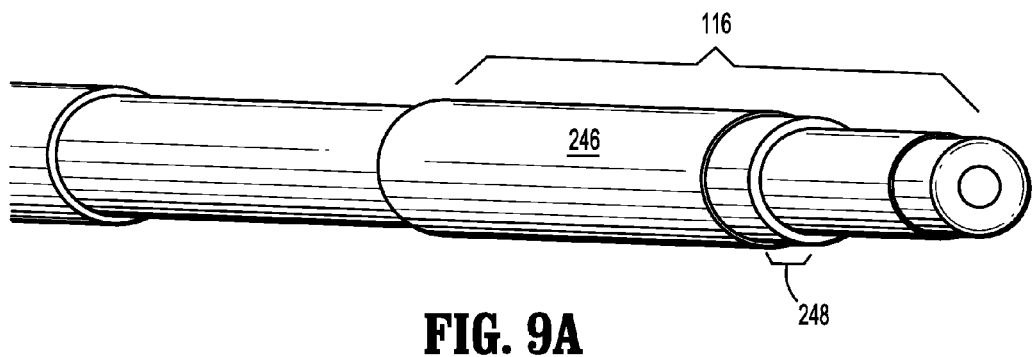
FIG. 9A is a perspective view of a coaxial cable assembly after performing still another step of the method of manufacturing the microwave applicator of FIGS. 2A-2D.
Figure 9B:
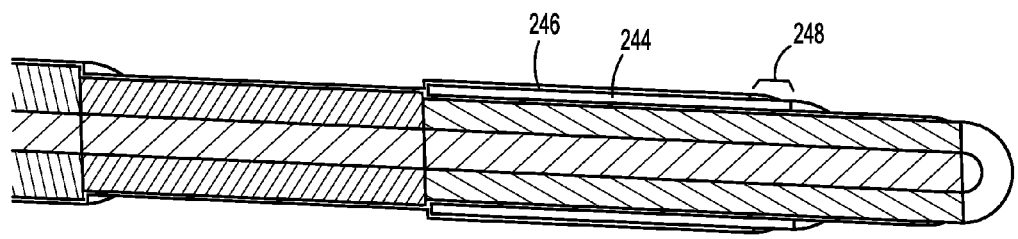
FIG. 9B is a longitudinal, cross-sectional view of the coaxial cable assembly of FIG. 9A.
Figure 10A:
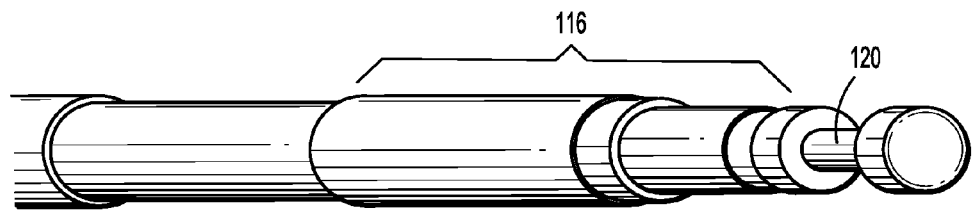
FIG. 10A is a perspective view of a coaxial cable assembly after performing still another step of the method of manufacturing the microwave applicator of FIGS. 2A-2D.
Figure 10B:
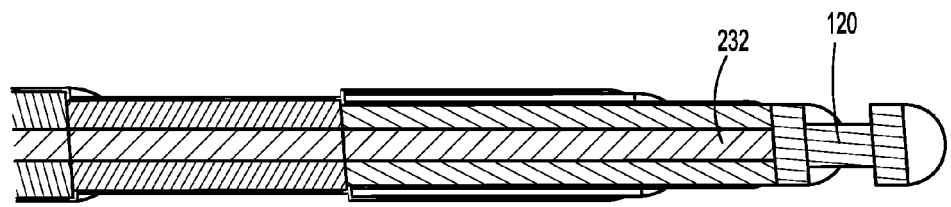
FIG. 10B is a longitudinal, cross-sectional view of the coaxial cable assembly of FIG. 10A.

Next, a balun insulator 244 is disposed around the proximal end of the third outer conductor 236 of the radiator base segment 116, as shown in FIGS. 8A and 8B. This may be accomplished by sliding a cylindrical balun insulator onto the proximal end of the third outer conductor 236. Next, a balun outer conductor 246 is disposed on the surface of a proximal portion of the balun insulator 244 leaving a distal portion of the balun insulator 244 exposed to form a feed gap 238, as shown in FIGS. 9A and 9B. Lastly, the distal radiating section 120 is attached to the distal end of the third inner conductor 232, as shown in FIGS. 10A and 10B. As shown in the figures, an electrical connection is made between the various outer conductors 216, 226, and 236 where they exist in proximity to one another, such as at the transitions between coaxial segments. The balun outer conductor 246 is also electrically connected at its proximal end to the coaxial outer conductors 226 and 236.

Another embodiment of the method of manufacturing a microwave applicator according to the stacking approach starts with a feed-line core (e.g., the feed-line core of FIG. 11A), including an inner conductor (e.g., inner conductor 1102) and insulator (e.g., insulator 1104). The insulator is stripped off of the distal length of the feed-line core equal to the length of the step-down segment and the radiator base segment. An insulator cylinder for the step-down segment is slid onto the inner conductor so that it is flush with the stripped feed-line insulator face. Next, an insulator cylinder of the radiator base segment is slid onto the inner conductor so that it is flush with the step-down insulator distal face. Hydrophilic gel, grease, or fluid may be applied between the faces of dielectric and onto the inner conductor to assist in slide assembly and to resist highly pressurized cooling fluid ingress into these spaces.

The braiding of the outer conductor over the stacked assembly would then be performed along the entire length of the stacked assembly. Conductive or dielectric ferrules may be added to the step faces of the insulator to improve the transition of the braid from one segment to the next, as shown in FIG. 13B. The braid is stripped back to form a feed gap on the radiator base segment. The balun insulator is then slid over, heat shrinked onto, or wrapped around the radiator base segment. A braid is placed over the balun insulator such that the proximal end of braid electrically shorts to the radiator base segment. A ferrule (choke short conductor) may be added to the proximal face of the balun dielectric to simplify electrical and mechanical termination of the balun braid. The balun braid is stripped back to expose the balun extended dielectric. Then, the distal radiating section 120 is attached to the radiator base segment's inner conductor 232. The distal radiating section 120 may be soldered, crimped, or welded to the radiator base segment's inner conductor 232. The antenna assembly is then slid into a cooling and dielectric buffering structure.

Figure 14:
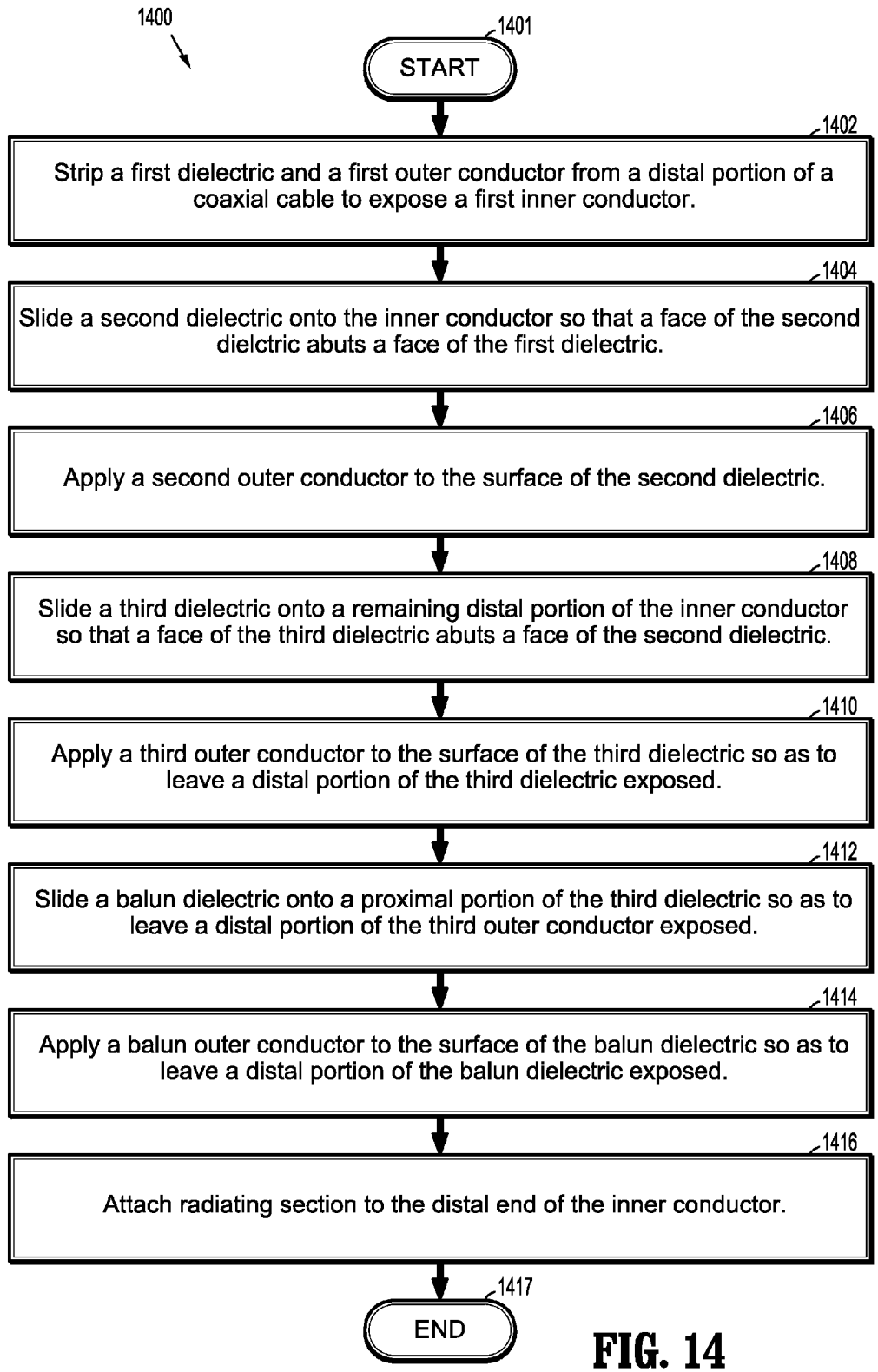
FIG. 14 is a flowchart of a method of manufacturing a microwave ablation applicator in accordance with an aspect of the present disclosure.

FIG. 14 illustrates a method of manufacturing a microwave applicator subassembly according to the stacking approach. After the method starts in step 1401, a first dielectric and a first outer conductor is stripped from a distal portion of a coaxial cable to expose a first inner conductor, in step 1402. In step 1404, a second dielectric is slid onto the inner conductor so that a proximal transverse face of the second dielectric abuts a distal transverse face of the first dielectric. In step 1406, a second outer conductor is applied to the surface of the second dielectric. In step 1408, a third dielectric is slid onto a remaining distal portion of the inner conductor so that a proximal transverse face of the third dielectric abuts a distal transverse face of the second dielectric. In step 1410, a third outer conductor is applied to the surface of the third dielectric so as to leave a distal portion of the third dielectric exposed.

In step 1412, a balun dielectric is slid onto a proximal portion of the third dielectric so as to leave a distal portion of the third outer conductor exposed. In step 1414, a balun outer conductor is applied to the surface of the balun dielectric so as to leave a distal portion of the balun dielectric exposed. Then, before the method ends in step 1417, the radiating section is attached to the distal end of the inner conductor, in step 1416.

Figure 11A:
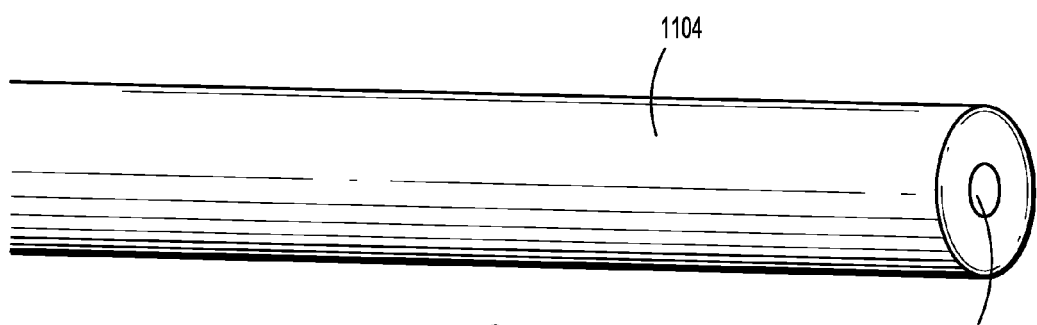
FIG. 11A is a perspective view of a partially completed coaxial cable assembly after performing a step of a method of manufacturing the partially completed coaxial cable assembly of FIGS. 7A and 7B in accordance with other aspects of the present disclosure.
Figure 11B:
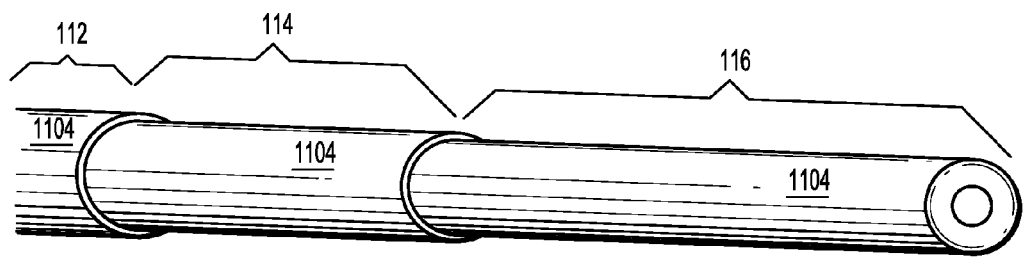
FIG. 11B is a perspective view of a partially completed coaxial cable assembly after performing another step of the method of manufacturing the partially completed coaxial cable assembly of FIGS. 7A and 7B.
Figure 11C:
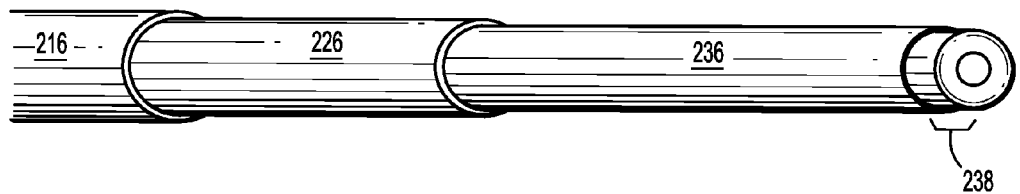
FIG. 11C is a perspective view of a partially completed coaxial cable assembly after performing still another step of the method of manufacturing the partially completed coaxial cable assembly of FIGS. 7A and 7B.

Alternatively, the microwave applicator may be manufactured by machining a coaxial feed-line core, which is illustrated in FIG. 11A. Starting with the coaxial feed-line core, which includes an inner conductor 1102 and insulator 1104, the insulator 1104 is machined down to a profile consistent with the geometries of the step-down segment 114 and radiator base segment 116, as shown in FIG. 11B. Then, as shown in FIG. 11C, a first outer conductor 216 is applied to the surface of the dielectric of the coaxial feed-line segment, a second outer conductor 226 is applied to the surface of the dielectric of the impedance step-down segment, and a third outer conductor 236 is applied to the surface of the proximal portion of the dielectric of the radiator base segment to leave the distal end of the dielectric exposed to form the feed gap 238. In other embodiments, an outer conductor is braided over the length of machined core profile. The braid is stripped back to form the feed gap 238.

The balun insulator 244 is then slid onto, heat shrinked onto, or wrapped over the radiator base segment 116. The balun conductor 246 is braided over the balun insulator 244 such that the proximal end of the balun conductor 246 electrically shorts to the radiator base segment 116. The balun braid is stripped back to expose a distal portion of the balun insulator 244. The distal radiating section 120 is then soldered, crimped, or welded onto the radiator base segment's inner conductor 232. Finally, the antenna assembly is slid into the cooling and dielectric buffering and cooling structure 122.

Figure 12:
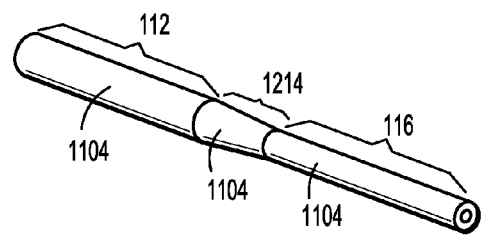
FIG. 12 is a perspective view of a partially completed coaxial cable assembly in accordance with still other aspects of the present disclosure.

In some embodiments, the coaxial feed-line core of FIG. 11A may be machined down to the geometry shown in FIG. 12, which tapers the diameter of the impedance step-down segment 1214. As shown in FIG. 12, the diameter of the impedance step-down segment 1214 tapers from a first diameter at a proximal end of the impedance step-down segment 1214 to a second smaller diameter at a distal end of the impedance step-down segment 1214.

Figure 13A:
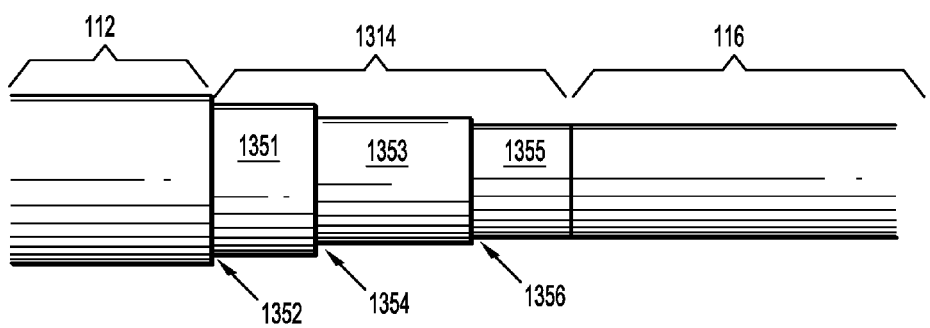
FIG. 13A is a side view of a partially completed coaxial cable assembly after performing a step of a method of manufacturing the partially completed coaxial cable assembly in accordance with still other aspects of the present disclosure.
Figure 13B:
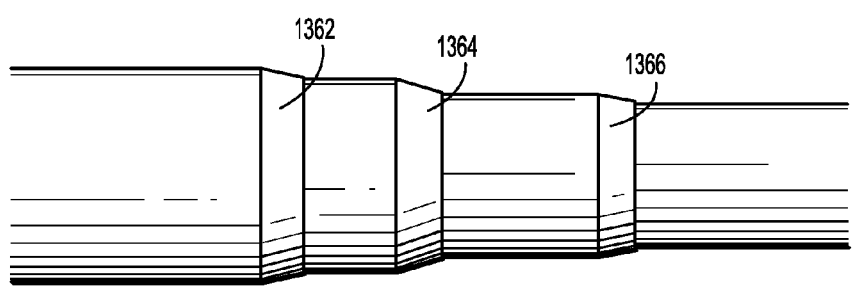
FIG. 13B is a side view of a partially completed coaxial cable assembly after performing another step of the method of manufacturing the partially completed coaxial cable assembly of FIG. 13A.

In other embodiments, the coaxial feed-line core of FIG. 11A may be machined down to the geometry shown in FIG. 13A. As shown, the impedance step-down segment 1314 includes multiple steps 1351, 1353, and 1355 having different diameters. Conductive or dielectric ferrules 1362, 1364, and 1366 may be disposed at the respective step faces 1352, 1354, and 1356 of respective steps 1351, 1353, and 1355 to provide a smooth transition between steps so that an outer conductor may be easily applied to the length of the microwave applicator.

Figure 15:
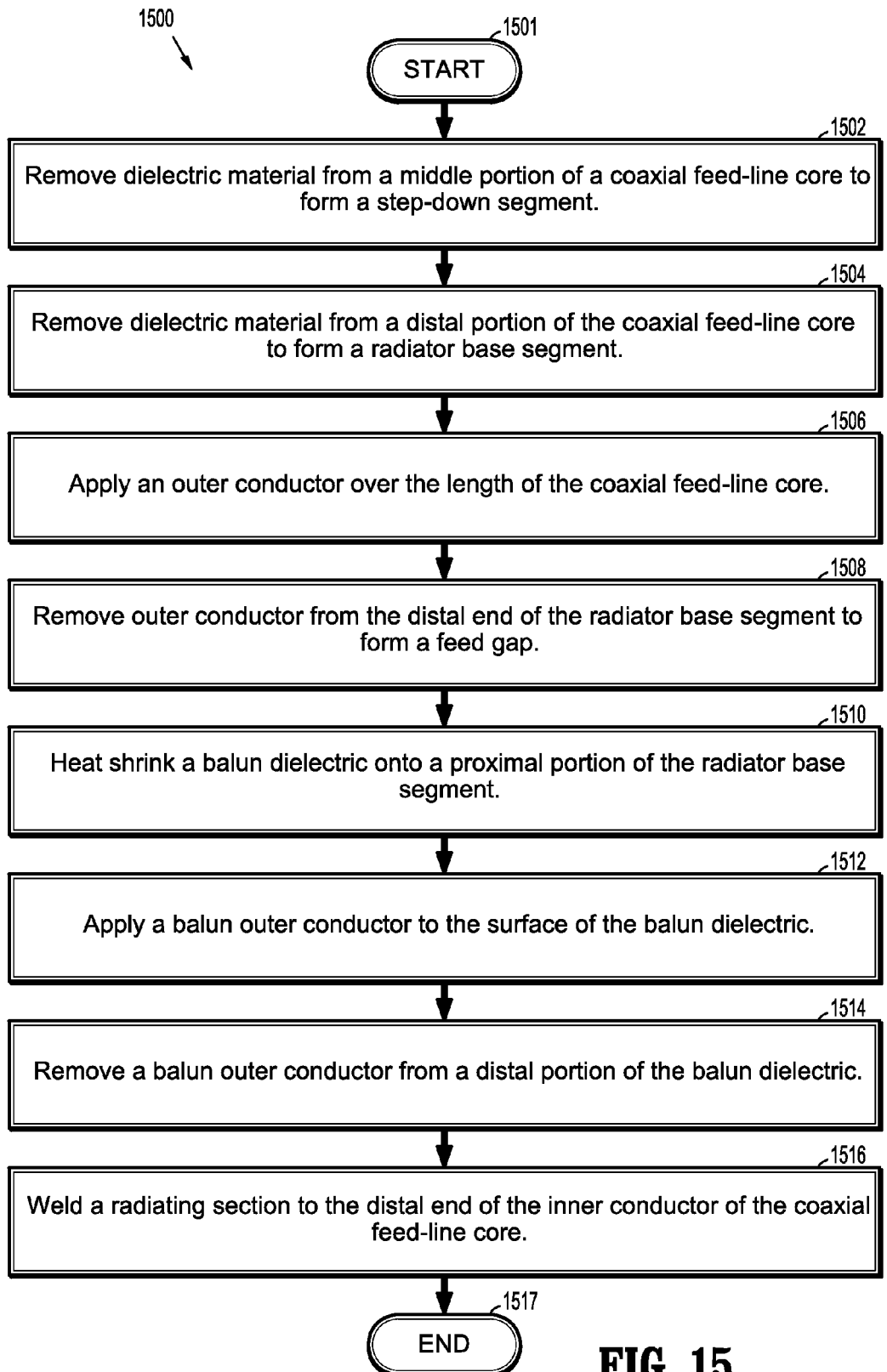
FIG. 15 is a flowchart of a method of manufacturing a microwave ablation applicator in accordance with another aspect of the present disclosure.

FIG. 15 illustrates a method 1500 of manufacturing a microwave applicator subassembly according to the machining approach. After the method starts in step 1501, dielectric material is removed from a middle portion of a coaxial feed-line core to form a step-down segment, in step 1502. In step 1504, dielectric material is removed from a distal portion of the coaxial feed-line core to form a radiator base segment. In step 1506, an outer conductor is applied over the length of the coaxial feed-line core. In step 1508, the outer conductor is removed from the distal end of the radiator base segment to form a feed gap. In step 1510, a balun dielectric onto a proximal portion of the radiator base segment. In step 1512, a balun outer conductor is applied to the surface of the balun dielectric. In step 1514, a balun outer conductor is removed from a distal portion of the balun dielectric. In step 1516, a radiating section is welded to the distal end of the inner conductor of the coaxial feed-line core. Then, in step 1517, the method of FIG. 15 ends.

As another alternative, the microwave applicator may be manufactured through selective removal of tape-wrapped dielectric. The profile of a tape-wrapped dielectric core could be made to match the described step-down segment profile by removing one or more layers of the tape along the appropriate length of the core. The remaining process would match the machining approach.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave ablation applicator comprising:
    a feed-line segment including a first inner conductor, a first dielectric disposed on an outer surface of the first inner conductor and having a first face in a plane perpendicular to a longitudinal axis of the first inner conductor, and a first outer conductor disposed on the outer surface of the first dielectric;
    a step-down segment adjacent to a distal end portion of the feed-line segment and including a second inner conductor, a second dielectric having a diameter less than a diameter of the first dielectric and disposed on the outer surface of the second inner conductor, and a second outer conductor disposed on the outer surface of the second dielectric; and
    a radiator base segment adjacent to a distal end portion of the step-down segment and including a third inner conductor, a third dielectric having a diameter less than the diameter of the first dielectric and disposed on the outer surface of the third inner conductor, a third outer conductor disposed on the outer surface of a proximal end portion of the third dielectric so as to form a feed gap at a distal end portion of the radiator base segment, a balun dielectric disposed on the outer surface of the third outer conductor, and a balun outer conductor disposed on the outer surface of the balun dielectric, the third outer conductor having a length that is less than a length of the third dielectric so as to form the feed gap,
    wherein a length of the step-down segment is based on a wavelength of an operation frequency of the microwave ablation applicator,
    wherein the balun outer conductor is directly connected to a proximal end portion of the third outer conductor,
    wherein the step-down segment includes multiple steps, and
    wherein a ferrule is disposed at each of the steps of the step-down segment.

2. The microwave ablation applicator according to claim 1, wherein one or more of the feed-line segment, the step-down segment, and the radiator base segment is rigid, semi-rigid, or flexible.

3. The microwave ablation applicator according to claim 1, wherein the diameter of the second and third inner conductors are equal to the diameter of the first inner conductor.

4. The microwave ablation applicator according to claim 1, wherein the second and third inner conductors are an extension of the first inner conductor.

5. The microwave ablation applicator according to claim 1, wherein the outer diameter of the balun outer conductor is equal to or approximately equal to the outer diameter of the first outer conductor of the feed-line segment.

6. The microwave ablation applicator according to claim 1, wherein the step-down segment tapers from a first diameter at a proximal portion of the step-down segment to a second smaller diameter at a distal portion of the step-down segment.

7. The microwave ablation applicator according to claim 1, wherein the length of the step-down segment is scaled by the dielectric constant of the second dielectric.

8. The microwave ablation applicator according to claim 1, wherein the feed-line segment, the step-down segment, and the radiator base segment are machined from a coaxial feed-line core including an inner conductor and a dielectric insulator disposed around the inner conductor.

9. The microwave ablation applicator according to claim 1, wherein at least one of the first dielectric, the second dielectric, the third dielectric, and the balun dielectric is dielectric tape.

10. The microwave ablation applicator according to claim 1, wherein the second dielectric is a foamed PTFE, low-density PTFE (LDPTFE), microporous PTFE, tape-wrapped PTFE, tape-wrapped and sintered PTFE, or PFA.

11. The microwave ablation applicator according to claim 1, wherein the second outer conductor is a silver-plated copper flat-wire braid, a solid-drawn copper tube, a conductive ink-coated PET heat shrink, a silver-coated PET heat shrink, or a silver-plated copper-clad steel braid.

* * * * *